United States Patent
Mathais et al.

[11] 3,972,874
[45] Aug. 3, 1976

[54] METHOD FOR PREPARING SYMMETRICAL AND UNSYMMETRICAL KETAZINES AND MIXTURES THEREOF

[75] Inventors: Henri Mathais, Sainte Foy les Lyon; Jean-Pierre Schirmann, Brignais; Francis Weiss, Pierre-Benite, all of France

[73] Assignee: Produits Chimiques Ugine Kuhlmann, Paris, France

[22] Filed: Dec. 9, 1974

[21] Appl. No.: 531,058

Related U.S. Application Data

[63] Continuation of Ser. No. 230,038, Feb. 28, 1972, abandoned.

[30] Foreign Application Priority Data
Mar. 11, 1971 France .............................. 71.08509

[52] U.S. Cl. .......................... 260/240 G; 260/566 B
[51] Int. Cl.² ..................................... C07C 109/00
[58] Field of Search ..................... 260/566 B, 240 G

[56] References Cited
FOREIGN PATENTS OR APPLICATIONS
708,339  5/1954  United Kingdom OTHER PUBLICATIONS
Brown et al, J. Am. Chem. Soc. vol. 77 pp. 1756–1759 (1955).

*Primary Examiner*—Gerald A. Schwartz
*Attorney, Agent, or Firm*—Pennie & Edmonds

[57] ABSTRACT

The invention relates to a method for preparing symmetrical ketazines of the formula

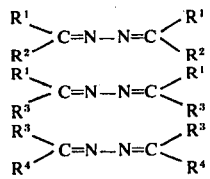

and unsymmetrical ketazines of the formula

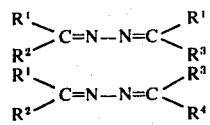

and mixtures of ketazines (I), (II) and (IV) and (I), (III) and (V) wherein $R^1$, $R^2$, $R^3$ and $R^4$ each is a straight chain alkyl radical of from 1 to 12 carbon atoms, a branched chain alkyl radical or cycloalkyl radical of from 3 to 12 carbon atoms, or a phenyl radical, the aforesaid radicals being unsubstituted or substituted with radicals which are stable in the medium in which the ketazines are prepared; and in which case $R^1$ and $R^2$ can be the same or different radicals, and $R^3$ and $R^4$ are radicals different from each other and are each a radical different from $R^1$ and $R^2$; or $R^1$ and $R^2$, or $R^1$ and $R^3$, or $R^3$ and $R^4$ of either or both the

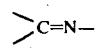

moieties together form a cyclic or substituted cyclic radical of from 3 to 11 carbon atoms in the ring, which comprises:

a. oxidizing a secondary alcohol of the formula

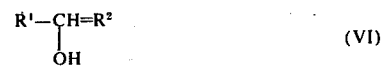

alone or together with a different secondary alcohol of the formula

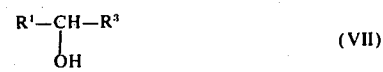

or

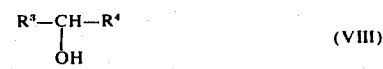

wherein $R^1$, $R^2$, $R^3$ and $R^4$ each has the same meaning as defined above, the oxidation to be carried out in the liquid phase employing molecular oxygen or a gaseous mixture containing the same, at a temperature and pressure which is sufficient to maintain the alcohol or alcohols in the liquid phase and result in a liquid phase mixture containing the peroxidic products of the auto-oxidation of the alcohol (VI) or the alcohols (VI) and (VII) or (VI) and (VIII);

b. reacting the peroxidic products with ammonia in the presence of cyanogen or a nitrile $R^5(CN)_n$ (IX) wherein $n$ is an integer of from 1 to 6 and $R^5$ is an unsubstituted or substituted saturated aliphatic, acyclic, or cyclic radical of from 1 to 12 carbon atoms or a phenyl or pyridinyl radical to result in the ketazine (I) or the mixture of ketazines (I), (II) and (IV) or (I), (III) and (V); and c. recovering the ketazine or mixture of ketazines.

15 Claims, No Drawings

METHOD FOR PREPARING SYMMETRICAL AND UNSYMMETRICAL KETAZINES AND MIXTURES THEREOF

This is a continuation of application Ser. No. 230,038, filed Feb. 28, 1972, now abandoned.

BACKGROUND OF THE INVENTION

I. Field of the Invention

This invention relates to a method for preparing symmetrical ketazines of the formula

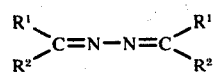  (I)

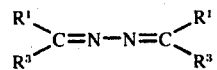  (II)

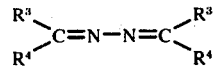  (III)

and unsymmetrical ketazines of the formula

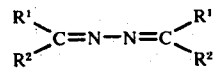  (IV)

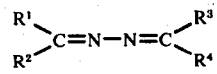  (V)

and mixtures of ketazines (I), (II), and (IV) or (I), (III) and (V) wherein $R^1$, $R^2$, $R^3$ and $R^4$ each has the same meaning designated above.

II. Description of the Prior Art

It is known that oxidation of a secondary alcohol in the liquid phase employing molecular oxygen as the oxidizing agent gives rise to mixtures containing peroxidic products of the auto-oxidation of the alcohol.

These mixtures of auto-oxidation products can contain in addition to the peroxidic products, a certain quantity of ketone and free hydrogen peroxide depending upon the reaction conditions and the particular alcohol used.

SUMMARY OF THE INVENTION

It has been surprisingly discovered that the reaction of the auto-oxidation products of one or more alcohols with ammonia in the presence of cyanogen or a nitrile results in the formation of ketazine (I) or mixture of ketazines (I) and (II) and (IV) or (I), (III) and (V).

When a single alcohol is reacted, the resulting ketazine will be a symmetrical ketazine; when two or more different alcohols are reacted, the resulting mixtures of ketazines will contain both symmetrical and unsymmetrical ketazines.

Broadly then, this invention relates to a method for preparing symmetrical ketazines of the formula:

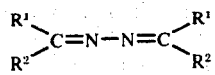  (I)

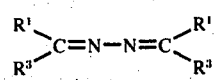  (II)

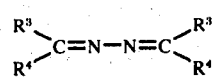  (III)

and unsymmetrical ketazines of the formula

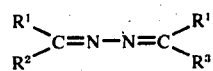  (IV)

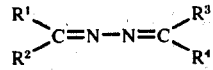  (V)

and mixtures of ketazines (I), (II) and (IV) and (I), (III) and (V) wherein $R^1$, $R^2$, $R^3$ and $R^4$ each is a straight chain alkyl radical of from 1 to 12 carbon atoms, a branched chain alkyl radical or cycloalkyl radical of from 3 to 12 carbon atoms, or a phenyl radical, the aforesaid radicals being unsubstituted or substituted with radicals which are stable in the medium in which the ketazines are prepared; and in which case $R^1$ and $R^2$ can be the same or different radicals, and $R^3$ and $R^4$ are radicals different from each other and are each a radical different from $R^1$ and $R^2$; or $R^1$ and $R^2$, or $R^1$ and $R^3$, or $R^3$ and $R^4$ of either or both the $$\text{>C=N-}$$

moieties together form a cyclic or substituted cyclic radical of from 3 to 11 carbon atoms in the ring, which comprises:

a. oxidizing a secondary alcohol of the formula $$R^1-\underset{\underset{OH}{|}}{CH}-R^2 \qquad (VI)$$

alone or together with a different secondary alcohol of the formula $$R^1-\underset{\underset{OH}{|}}{CH}-R^3 \qquad (VII)$$

or $$R^3-\underset{\underset{OH}{|}}{CH}-R^4 \qquad (VIII)$$

wherein $R^1$, $R^2$, $R^3$ and $R^4$ each has the same meaning as defined above, the oxidation to be carried out in the liquid phase employing molecular oxygen or a gaseous mixture containing the same, at a temperature and pressure which is sufficient to maintain the alcohol or alcohols in the liquid phase and result in a liquid phase mixture containing the peroxidic products of the auto-oxidation of the alcohol (VI) or the alcohols (VI) and (VII) or (VI) and (VIII);

b. reacting the peroxidic products with ammonia in the presence of cyanogen or a nitrile $R^5(CN)_n$ wherein $n$ is an integer from 1 to 6 and $R^5$ is an unsubstituted or substituted saturated aliphatic, acyclic, or cyclic radical of from 1 to 12 carbon atoms or a phenyl or pyridinyl radical to result in the ketazine (I) or the mixture of ketazines (I), (II) and (IV) or (I), (III) and (V);

c. recovering the ketazine or mixture of ketazines.

DESCRIPTION OF THE PREFERRED EMBODIMENTS

Some examples of secondary alcohols conforming to formulas (II), (VII) and (VIII) which are advantageous in carrying out the process of this invention include isopropanol, 2-butanol, 2-pentanol, 3-pentanol, 3-methyl-2-butanol, 4-methyl-2-pentanol, 2-octanol, 1-cyclohexylethanol, 1-phenylethanol, diphenylcarbinol, cyclobutanol, cyclopentanol, cyclohexanol, 2-methylcyclohexanol, 3-methylcyclohexanol, 3,3,5-trimethylcyclohexanol, cycloheptanol, cyclooctanol and cyclododecanol.

As will be readily understood by one skilled in the art, many other secondary alcohols in addition to those specifically recited herein can be employed in the process of this invention. Moreover the alcohol or alcohols chosen can contain substituents which are stable in the reaction medium, as for example, methyl, methoxy, chloro, fluoro, or nitro groups.

The nitriles conforming to formula (IX) which can be advantageously employed in the practice of this invention include the mononitriles and polynitriles wherein the radical $R^5$ is a hydrocarbon radical containing up to 12 carbon atoms, which hydrocarbon radical can be a cyclic or acyclic radical or an aromatic radical such as a phenyl or pyridinyl radical. Moreover the radical $R^5$ can contain from 1 to 6 substituents advantageously selected from amongst those groups which are not susceptible to oxidation under the conditions of the reaction, as for example, carbamyl, carboxylic, carboxylic ester, nitro, primary amine, secondary amine, tertiary amine, nitroso, fluoro, chloro, bromo, iodo, hydroxy, ether, acetal, epoxy, sulfoxide, sulfur, sulfone and sulphonic acid groups.

In addition to cyanogen, specific examples of formula (IX) nitriles which are advantageously employed according to this invention include acetonitrile, propionitrile, butyronitrile, isobutyronitrile, cyclohexylcarboxylic nitrile, benzonitrile, tolunitriles, the cyanopyridines, the mono-, di- and trichloroacetonitriles, m-chlorobenzonitrile, p-methoxybenzonitrile, p-nitrobenzonitrile, m-trifluoromethylbenzonitrile, glycolonitrile, epsilonhydroxycapronitrile, cyanoacetic acid, the amides and alkyl esters of cyanoacetic acid, the amide and alkyl esters of beta-cyanopropionic acid, malononitrile, succinonitrile, glutaronitrile, adiponitrile, pimelonitrile, suberonitrile, the phthalonitriles and the nitriles which are prepared from the cyanoethylation with acrylonitrile or methacrylonitrile of water, an alcohol, a polyol and a carboxylic acid.

Examples of nitriles prepared from cyanoethylation include betahydroxypropionitrile, β,β'-oxydipropionitrile, the β-alkoxypropionitriles such as β-methoxypropionitrile, the cyanoethylation products of ethyleneglycol, propyleneglycol, glycerol and sorbitol. Certain of these nitriles can be formed in situ depending upon the constituents of the reaction medium, most notably, water or alcohol, by the reaction of acrylonitrile or methacrylonitrile thus permitting the use of these ethylenic nitriles as starting materials in the process of this invention.

In addition to ketazines (I) the process of this invention can result in generally small quantities of derivatives of hydrazine and ketone, notably a diaziridine of the formula:

and a hydrazone of the formula

Similarly, when a mixture of ketazines (I), (II) and (IV) or (I), (III) and (V) are prepared, the process of this invention can also result in a mixture of diaziridines and hydrazones wherein the "R" substituents of these by-products correspond to the "R" substituents of the starting mixture of alcohols.

The formation of diaziridines and hydrazones with ketazines is such an integral feature of this invention that for the sake of simplicity, the invention is referred to as a method for preparing symmetrical and unsymmetrical ketazines and mixtures thereof.

The auto-oxidation of the secondary alcohol or mixture of secondary alcohols can be carried out in known and conventional ways. The alcohol or mixture thereof is contacted with molecular oxygen or with a gas containing oxygen, as for example, air, under such conditions of pressure and temperature that the alcohol or mixture of alcohols as well as the peroxidic compounds, ketone(s) and hydrogen peroxide resulting from the auto-oxidation reaction will be in the liquid phase.

The temperature of the reaction can be maintained between about 60° and 180°C and advantageously between about 80° and 160°C. The reaction can be made to take place at atmospheric pressure if the nature of the starting materials and the temperature selected for the reaction permit. This reaction can also be made to take place at a pressure higher than the atmospheric pressure, for example, up to 50 atmospheres, if such pressure is necessary to maintain the reaction products in the liquid phase.

The reaction medium should be kept free of any heavy metal ions which risk catalyzing the decomposition of the perodicic compounds. It is therefore advantageous to take such precautions to prevent the presence of these ions as the addition of agents to the reaction medium capable of sequestering the ions, for example, an alkaline phosphate and the use of inert materials for the construction of the oxidation reactor, for example, glass, enamelled steel, stainless steel, and so forth.

It is known that the initiation of the oxidation reactions, using oxygen can be facilitated by the addition of substances to the reaction medium which give rise to free radicals, for example, the ketone peroxides, hydrogen peroxide, tertiobutyl peroxide and azobisisobutyronitrile. If desired, the aforesaid substances may be added to the secondary alcohol or mixture thereof, for example, at a level of about 0.01 to 2% by weight.

The reaction can be carried out batch-wise or continuously.

The oxidation of secondary alcohol is continued until from about 5 to 30% of the alcohol is transformed. A much lower level of transformation can be employed, however, such is generally uneconomical. Similarly, while it is possible to reach the upper limit of transformation indicated above, it is known in this case that the selectivity of the reaction for the formation of peroxides is diminished and that there is a risk of attaining concentration of peroxides presenting the dangers of an explosion. The optimum level for the transformation should be selected bearing in mind the type of alcohol or alcohols employed and the operating conditions, factors which determine the stability of the peroxidic compounds.

While it is within the scope of this invention to concentrate the peroxidic products by suitable means, as by removing the unreacted alcohol, it is advantageous for reasons of economy and safety to utilize the mixture resulting from the oxidation of secondary alcohol as is in the following step of oxidizing with ammonia in the presence of a nitrile.

An advantageous manner of carrying out the second oxidizing step of the method of this invention comprises mixing the crude product resulting from the first oxidizing step with ammonia and the nitrile and carrying out the reaction at a temprature between about 0° and 100° for a period of time which is sufficient to consume the greater part of the peroxidic oxygen present in the reaction medium.

The second oxidizing step can be carried out in the presence of water or a solvent in order to facilitate the homogenization of the mixture. The solvent can advantageously be an alkyl monoalcohol containing 1 to 4 carbon atoms, as for example, methanol, ethanol, n-propanol, isopropanol, n-butanol, sec-butanol, isobutanol and tert-butanol.

The quantity of ammonia employed can advantageously be between about 0.2 and 5 moles per equivalent of peroxidic oxygen. The nitrile can be employed at a level of from about 1 to 10 moles per equivalent of peroxidic oxygen. If desired, one can add a quantity of ketone or ketone in the form of the peroxide corresponding to the starting alcohol ot the reaction medium to add to the quantity of ketone contained therein. This additional quantity of ketone can be added at a level of from 1 to 2 moles per equivalent of peroxidic oxygen.

The ammonia utilized can be anhydrous or in aqueous solution. In the case of the latter, it is advantageous to employ a 15% concentration of $NH_3$ by weight.

It is advantageous to add from about 0.01 to 1% by weight of an agent to the mixture of the peroxidic products which will stabilize the peroxides and hydrogen peroxide, as for example, phosphoric acid, nitrilotriacetic acid, ethylenediamunetetraacetic acid and the sodium salts of the aforesaid acids. It is also advantageous to add a catalyst such as an ammonium or alkaline metal salt, especially a lithium, sodium or potassium salt of a hydracid, mineral oxyacid, aromatic or aliphatic carboxylic acid or alkyl or arylsulfonic acid containing less than about 20 carbon atoms, and wherein the anions are stable under the oxidizing conditions of the reaction medium. Examples of such catalysts include the ammonium or alkaline metal whose anions are: fluoride, chloride, sulfate, nitrate, phosphate, pyrophosphate, borate, carbonate, formate, acetate, propanate, butyrate, isobutyrate, hexanoate, octanoate, dodecanoate, stearate, oxalate, succinate, glutarate, adipate, benzoate, phthalate, methanesulfonate, ethanesulfonate, benzene sulfonate, p-toluenesulfonate and so forth. These salts can be employed as is or in the case of the ammonium salts, the salt can be generated in situ by the addition of the appropriate acid to the reaction medium containing ammonia. The quantity of salt employed is advantageously from about 0.01 to 2% by weight of the total reaction medium.

Upon completion of the second oxidizing step of the method of this invention the ketazine or mixture of ketazines as the case might be are recovered employing known and conventional methods, as for example, by extraction with a non-miscible solvent, fractional distillation or a combination of extraction and distillation.

Ketazines are very useful as intermediate products for a variety of syntheses, particularly in the manufacture of hydrazine and numerous organic nitrogen compounds employed as pesticides or as pharmaceutical products. In the manufacture of hydrazine, for example, ketazines can be reacted with water and/or a strong acid to produce hydrazine hydrate and/or a hydrazine salt. The hydrazine hydrate and/or hydrazine salt are readily converted to hydrazine employing well known processes.

The following examples are illustrative of the method of this invention:

Glass apparatus equipped with mechanical agitation and refrigeration means was employed throughout.

EXAMPLE 1

280 gm. of cyclohexanol and 2.8 gm. of cyclohexanone peroxide obtained from the reaction of cyclohexanone with oxygen in the presence of a small amount of hydrochloric acid were placed in a glass reactor of 500 $cm^3$ volume and equipped with a rapid stirrer. 300 $cm^3$ of oxygen per minute were bubbled into the reaction medium through a tube fitted with a fritted glass disc and the reaction medium was heated to a temperature of from 120°–125°C. After 45 minutes, this operation was stopped and the reaction medium measured 0.31 equivalents of peroxidic oxygen or a level of transformation of 11% of the starting cyclohexanol.

A solution of 40 gm. of benzonitrile (0.39 moles), 17 gm. ammonia (1 mole) and 0.5 gm. of the disodium salt of ethylenediamine tetraacetic acid in 100 gm. of methanol were then added to the mixture of peroxidic products over a period of 1 hour during which the temperature was maintained at 40°C. The reaction was left to proceed for 3 hours after which analysis by gas phase chromatography indicated that the medium contained 31 gm. of cyclohexanoneazine (0.16 mole).

The solution was then concentrated under a pressure of 200 mm. Hg until the boiling temperature reached 50°C., followed by a pressure of 10 mm. Hg until the boiling temperature reached 100°C. The residue was extracted with chloroform and the resulting extract was dried over anhydrous sodium sulfate and subjected to distillation. In this manner, 26 gm. of cyclohexanoneazine boiling at 87°–88°C. under 0.2 mm. Hg and crystallizing at a freezing point of 37°C. were obtained. This product possessed an infrared spectrum which is identical to that published in the literature (Anal. Chem 1964, 36 (7), 1349) with a characteristic band of C=N of 1640 $cm^{-1}$.

EXAMPLE 2

In a first step, isopropanol was oxidized with air in an agitated glass reactor resistant to pressure and equipped with an air-injection tube as well as a reflux condensor through which the residual gases could escape.

300 gm. of isopropanol, 15 gm. of acetone and 10 gm. of a 70% by weight aqueous solution of hydrogen peroxide were placed in the reactor and 300 cm³ of air per minute under a pressure of 3 bars at a temperature of 105°–110°C. were bubbled in until the solution contained an amount of peroxidic product corresponding to 1.1 equivalents of peroxidic oxygen.

A solution of 57 gm. of acetonitrile (1.1 moles), 58 gm. of acetone (1 mole), 50 gm. ammonia (3moles) and 0.5 gm. of disodium salt of ethylenediaminetetraacetic acid and a solution of 0.1 gm. ammonium acetate in 400 gm. methanol were introduced into the reactor over a period of one hour while the temperature was maintained at 50°C. The reaction was then continuously heated at 50°C. for 6 hours during which a light stream of gaseous ammonia (5 gm./hour–0.3 moles/hour) was bubbled into the reactor. At the end of the reaction, measurement by gas phase chromatography showed the presence of 84 gm. acetoneazine (0.75 moles) in the reaction medium.

The excess ammonia was driven off by evaporation under vacuum and the entire distillate comprising solvents and volatile reactants, that is to say methanol, isopropanol, acetonitrile and unreacted acetone, was distilled under 200 mm. Hg. and finally, the acetoneazine present as an azeotrope with water was distilled under 50 mm. Hg. In this manner, 166 gm. of 47.5% by weight aqueous solution of acetoneazine containing 79 gm. of pure acetoneazine (0.71 moles) were obtained.

We claim:

1. A method for preparing symmetrical ketazines of the formula

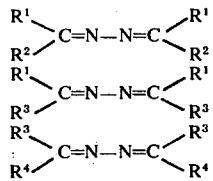

and unsymmetrical ketazines of the formula

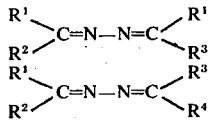

and mixtures of ketazines wherein $R^1$, $R^2$, $R^3$ and $R^4$ are each a straight chain alkyl radical of from 1 to 12 carbon atoms, a branched chain alkyl radical or cycloalkyl radical of from 3 to 12 carbon atoms, or a phenyl radical, the aforesaid radicals being unsubstituted or substituted with one or more halogen atoms or methyl, methoxy or nitro groups; $R^1$ and $R^2$ can be the same or different radicals, and $R^3$ and $R^4$ are radicals different from each other and are each a radical different from $R^1$ and $R^2$; or $R^1$ and $R^2$, or $R^1$ and $R^3$, or $R^3$ and $R^4$ together form an alkylene radical of from 3 to 11 carbon atoms, said alkylene radical being unsubstituted or substituted with one or more halogen atoms or methyl, methoxy or nitro groups, which comprises:

a. oxidizing a secondary alcohol of the formula

alone or together with a different secondary alcohol of the formula

or

wherein each of $R^1$, $R^2$, $R^3$ and $R^4$ has the same meaning as defined above, in the liquid phase employing molecular oxygen or a gaseous mixture containing the same, at a temperature and pressure which is sufficient to maintain the alcohol or alcohols in the liquid phase to produce a mixture containing the peroxidic products of the auto-oxidation of the alcohols in the liquid phase;

b. reacting the peroxidic products with ammonia in the presence of cyanogen or a nitrile $R^5(CN)_n$ (IX) wherein $n$ is an integer of from 1 to 6 and $R^5$ is a straight chain alkyl radical of from 1 to 12 carbon atoms, a branched chain alkyl radical or cycloalkyl radical of from 3 to 12 carbon atoms or a phenyl or pyridinyl radical, the aforesaid radicals being unsubstituted or substituted with from 1 to 6 halogen atoms or carbamyl, carboxylic, nitro, amino, nitroso, hydroxy or sulfonic acid groups, to produce the ketazine or mixture of ketazines; and c. recovering the ketazine or mixture of ketazines.

2. The method of claim 1 wherein the secondary alcohols (VI), (VII), and (VIII) are selected from isopropanol, 2-butanol, 2-pentanol, 3-pentanol, 3-methyl-2-butanol, 4-methyl-2-pentanol, 2-octanol, cyclohexylethanol, 1-phenylethanol, diphenylcarbinol, cyclobutanol, cyclopentanol, cyclohexanol, 2-methylcyclohexanol, 3-methylcyclohexanol, 3,3,5-trimethylcyclohexanol, cycloheptanol, cyclooctanol and cyclododecanol and mixtures thereof.

3. The method of claim 1 wherein the nitrile is acetonitrile, propionitrile, butyronitrile, isobutyronitrile, cyclohexylcarboxylic nitrile, benzonitrile, a tolunitrile, a cyanopyridine, a mono-, di-, or trichloroacetonitrile, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, an amide or alkyl ester of cyanoacetic acid, an amide or alkyl ester of beta-cyanopropionic acid, malononitrile, succinonitrile, glutaronitrile, adiponitrile, pimelonitrile, suberonitrile, a phthalonitrile, betahydroxypropionitrile, $\beta,\beta'$-oxydipropionitrile, a $\beta$-alkoxypropionitrile or a nitrile obtained by cyanoethylation with acrylonitrile or methacrylonitrile of ethyleneglycol, propyleneglycol, glycerol or sorbitol.

4. A method of claim 1 wherein the temperature of step (a) is maintained between about 80° and 160°C.

5. The method of claim 1 wherein an alkaline phosphate is added to the reaction medium as a sequestering agent.

6. The method of claim 1 wherein a ketone peroxide, hydrogen peroxide, tertiobutyl peroxide or azobisisobutyronitrile is added to the alcohol or alcohols of step (a) at a level of about 0.01 to 2% by weight.

7. The method of claim 1 wherein unreacted alcohol is removed from the mixture of peroxidic products before the mixture is subjected to step (b).

8. The method of claim 1 wherein step (b) is carried out in the presence of a dissolving amount of an alkyl mono-alcohol containing 1 to 4 carbon atoms.

9. The method of claim 1 wherein the ammonia is utilized at a level of from about 0.2 to 5 moles per equivalent of peroxidic oxygen.

10. The method of claim 1 wherein the nitrile (IX) is utilized at a level of from about 1 to 10 moles per equivalent of peroxidic oxygen.

11. The method of claim 1 wherein a ketone or ketone peroxide corresponding to the starting alcohol is added at a level of from 1 to 2 moles per equivalent of peroxidic oxygen.

12. The method of claim 1 wherein from about 0.01 to 1% by weight of a stabilizer is added to the mixture of peroxidic products of step (a).

13. The method of claim 1 wherein from about 0.01 to 2% by weight of an ammonium or alkaline metal salt of a hydracid, mineral oxyacid, aromatic or aliphatic carboxylic acid or alkyl or arylsulfonic acid containing less than about 20 carbon atoms and wherein the anions are stable under the oxidizing conditions of the reaction medium is added as a catalyst.

14. The method of claim 1 wherein the temperature of step (b) is maintained between about 0° and 100°C.

15. A method for preparing ketazines which comprises:
   a. oxidizing a secondary alcohol selected from isopropanol, 2-butanol, 2-pentanol, 3-pentanol, 3-methyl-2-butanol, 4-methyl-2-pentanol, 2-octanol, 1-cyclohexylethanol, 1-phenylethanol, diphenylcarbinol, cyclobutanol, cyclopentanol, cyclohexanol, 2-methylcyclohexanol, 3-methylcyclohexanol, 3,3,5-trimethylcyclohexanol, cycloheptanol, cyclooctanol and cyclododecanol and mixtures thereof, in the liquid phase employing molecular oxygen or a gaseous mixture containing the same, at a temperature and pressure which is sufficient to maintain the alcohol or mixture of alcohols in the liquid phase to produce a mixture containing the peroxidic products of the auto-oxidation in the liquid phase;
   b. reacting the peroxidic products with ammonia in the presence of cyanogen or a nitrile selected from acetonitrile, propionitrile, butyronitrile, isobutyronitrile, cyclohexylcarboxylic nitrile, benzonitrile, a tolunitrile, a cyanopyridine, the mono-, di- and trichloroacetonitriles, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, the amide and alkyl esters of cyanoacetic acid, the amide and alkyl esters of beta-cyanopropionic acid, malononitrile, succinonitrile, glutaronitrile, adiponitrile, pimelonitrile, suberonitrile, a phthalonitrile, betahydroxypropionitrile, $\beta,\beta'$-oxydipropionitrile, a $\beta$-alkoxypropionitrile and nitriles obtained by cyanoethylation with acrylonitrile or methacrylonitrile of ethyleneglycol, propyleneglycol, glycerol or sorbitol; and
   c. recovering the ketazine or mixture of ketazines.

* * * * *

UNITED STATES PATENT AND TRADEMARK OFFICE
CERTIFICATE OF CORRECTION

PATENT NO. : 3,972,874
DATED : August 3, 1976
INVENTOR(S) : Henri Mathais et al.

It is certified that error appears in the above-identified patent and that said Letters Patent are hereby corrected as shown below:

In Abstract, Column 2, Formula (VI) 

should be $--R^1-\underset{\underset{OH}{|}}{CH}-R^2--$

Column 4, line 55 "perodidic" should be --peroxidic--

Column 5, line 47 "ot" should be --to--

Signed and Sealed this

Twelfth Day of April 1977

[SEAL]

Attest:

RUTH C. MASON
*Attesting Officer*

C. MARSHALL DANN
*Commissioner of Patents and Trademarks*